United States Patent
Neuwirth et al.

(10) Patent No.: US 8,042,548 B2
(45) Date of Patent: Oct. 25, 2011

(54) OCCLUSION OF FALLOPIAN TUBES

(75) Inventors: Robert S. Neuwirth, Englewood, NJ (US); Michel Gensini, Flemington, NJ (US)

(73) Assignee: Ethicon, Inc., Somerville, NJ (US), part interest ( * ) Notice: Subject to any disclaimer, the term of this patent is extended or adjusted under 35 U.S.C. 154(b) by 0 days.

(21) Appl. No.: 12/084,185

(22) PCT Filed: Oct. 27, 2006

(86) PCT No.: PCT/US2006/041700
§ 371 (c)(1), (2), (4) Date: Apr. 25, 2008

(87) PCT Pub. No.: WO2007/053401
PCT Pub. Date: May 10, 2007

(65) Prior Publication Data
US 2009/0155367 A1  Jun. 18, 2009

(51) Int. Cl.
A61F 6/06 (2006.01)
A61F 13/20 (2006.01)
A61B 17/42 (2006.01)

(52) U.S. Cl. .......... 128/831; 606/119; 604/11; 424/430

(58) Field of Classification Search .......... 128/830–832, 128/833; 604/11, 13, 48, 515; 606/119, 606/134; 424/423, 424, 426, 430, 431, 2.1, 424/2.14, 2.21
See application file for complete search history.

(56) References Cited

U.S. PATENT DOCUMENTS

| | | | | |
|---|---|---|---|---|
| 3,374,788 A | * | 3/1968 | Rosenthal | 128/840 |
| 3,991,760 A | * | 11/1976 | Drobish et al. | 128/832 |
| 4,185,618 A | * | 1/1980 | Corey | 128/831 |
| 5,073,365 A | * | 12/1991 | Katz et al. | 427/2.24 |
| 6,602,261 B2 | * | 8/2003 | Greene et al. | 606/108 |
| 2005/0171569 A1 | * | 8/2005 | Girard et al. | 606/193 |

FOREIGN PATENT DOCUMENTS

WO    WO2004093793    *    4/2004

* cited by examiner

Primary Examiner — Patricia Bianco
Assistant Examiner — Tarla Patel
(74) Attorney, Agent, or Firm — Olson & Cepuritis, Ltd.

(57) ABSTRACT

A method for inducing Fallopian tube blockage as a means for female contraception comprises contacting the inner surface tissue of a Fallopian tube with a silver nitrate bearing substrate and delivering an amount of silver nitrate to the tissue sufficient to induce blockage of the Fallopian tube. At least one silver nitrate bearing bead is introduced through the uterine opening of the Fallopian tube by use of a catheter or other device suitable for manipulating the bead. Alternatively, a plurality of beads can be introduced into the Fallopian tube. In a preferred embodiment, one or more silver nitrate bearing beads are arranged on a string to facilitate later removal of the beads. The method of the present invention delivers an amount of silver nitrate to the tissue sufficient to cause tissue necrosis and blockage of the Fallopian tube.

20 Claims, 5 Drawing Sheets

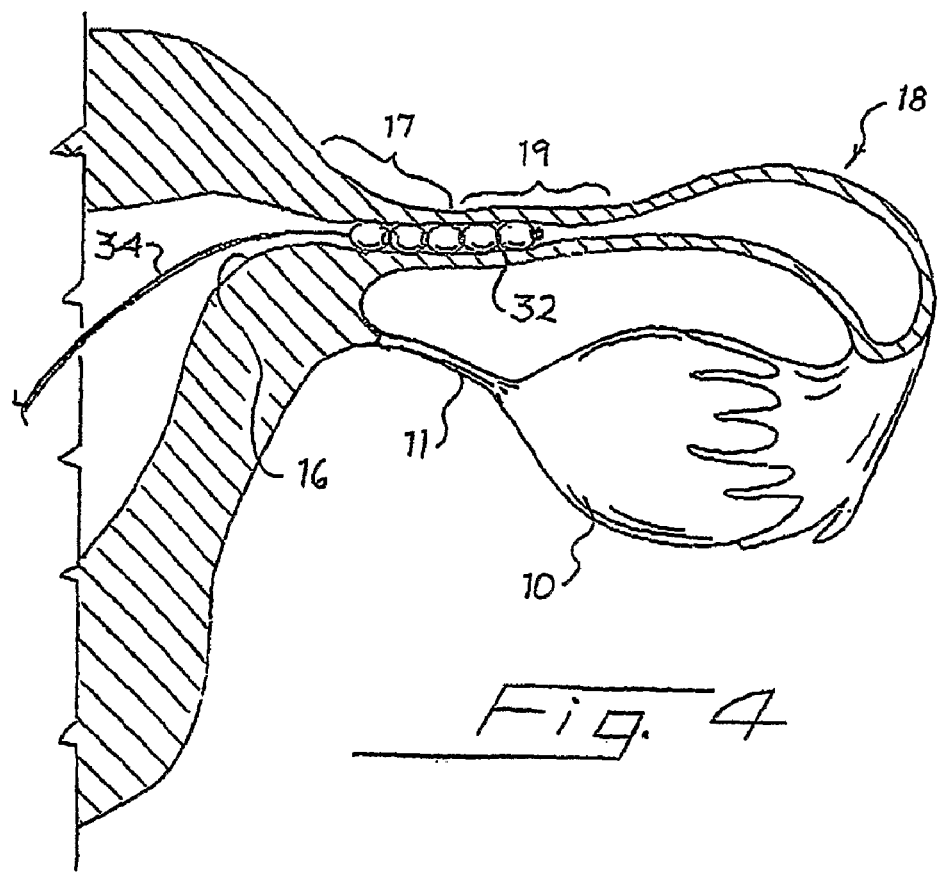
Fig. 4
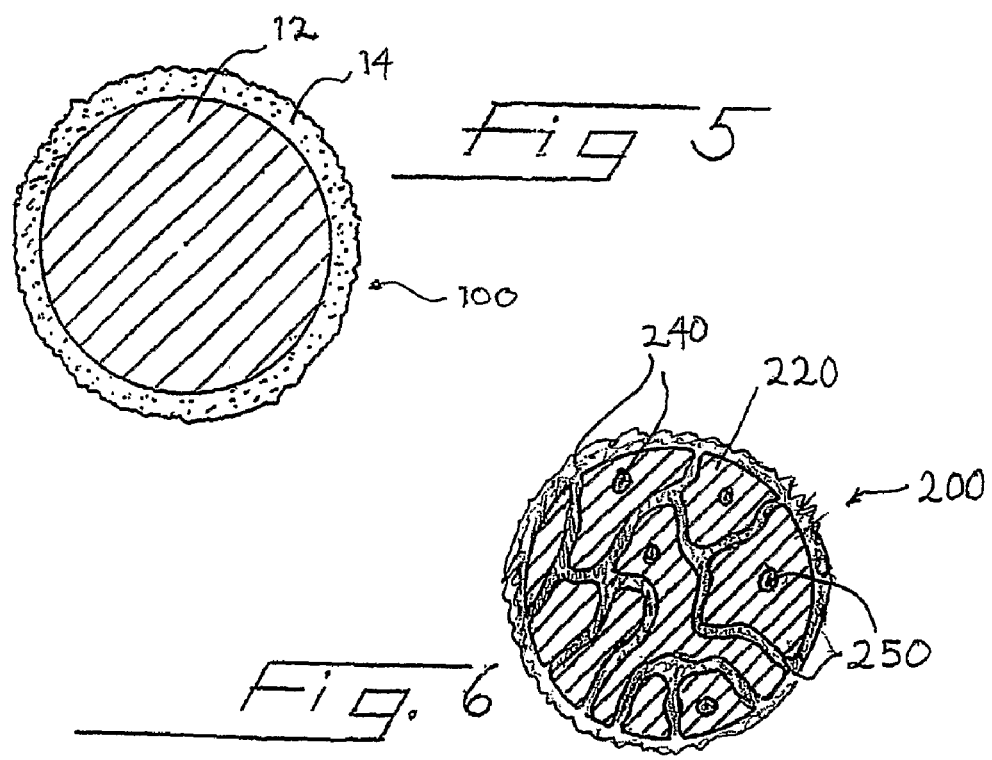
Fig. 5
Fig. 6

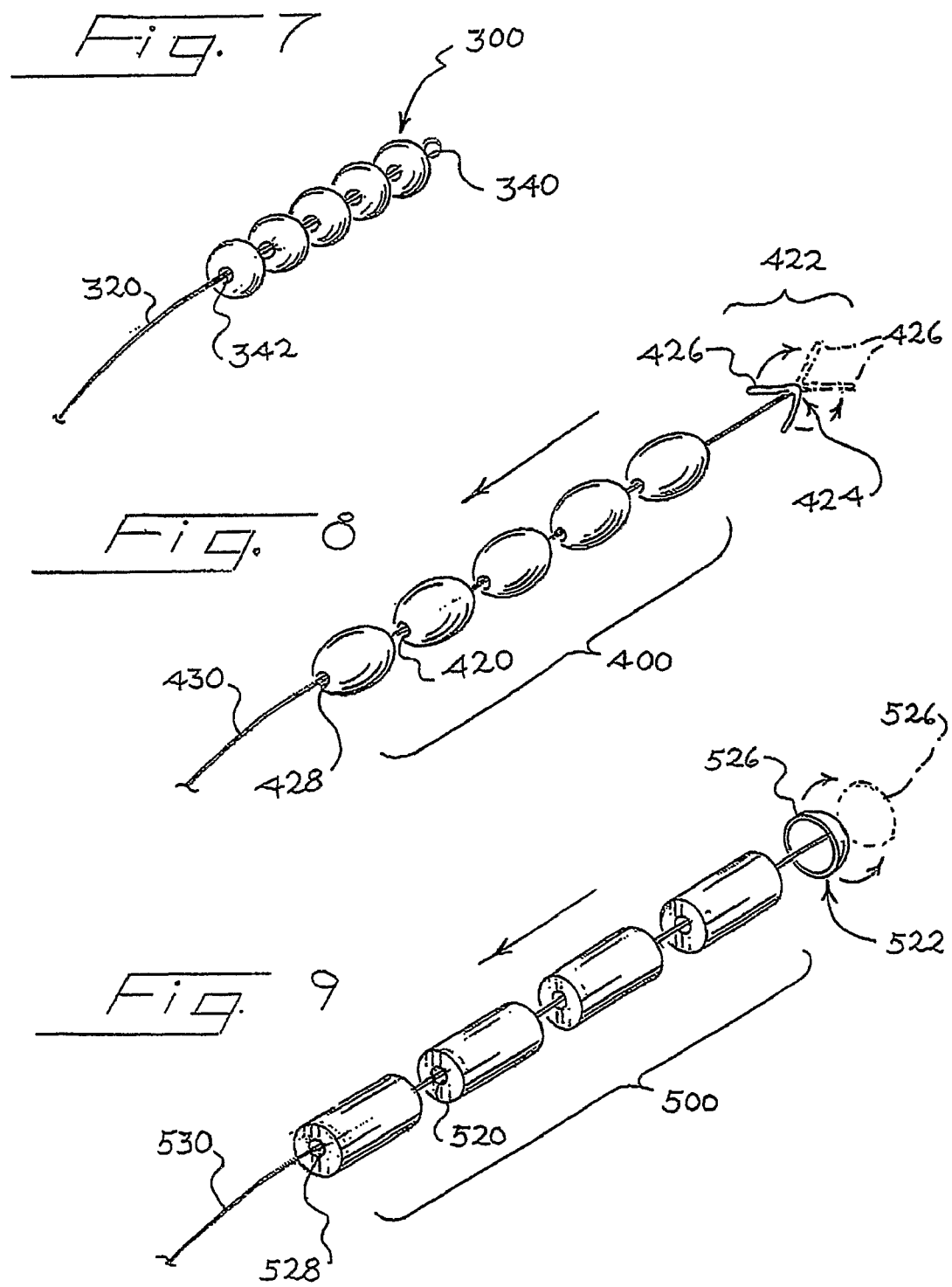

OCCLUSION OF FALLOPIAN TUBES

FIELD OF THE INVENTION

This invention relates generally to methods and devises for chemical sterilization of a female patient. More particularly, this invention relates to methods for delivering tissue necrosing silver nitrate to Fallopian tubes of a patient to occlude the Fallopian tubes and thereby induce sterility.

BACKGROUND OF THE INVENTION

Female sterilization is one of the most common forms of birth control used today. Procedures for female sterilization fall into two broad categories: surgical and chemical. Surgical sterilization procedures almost universally require surgical ligation of the Fallopian tubes or occlusion of the Fallopian tubes by application of clips to the exterior of the tubes. Ligation and clipping procedures generally involve making a surgical incision in the abdomen to access the Fallopian tubes. This is a costly procedure that must be performed by a skilled surgeon in a hospital setting. Like any surgical intervention, there are risks of infection involved with surgical sterilization. Such procedures are often not a viable option for women in developing countries, where the cost is prohibitive, post-operative monitoring may be difficult, and availability of surgeons and facilities to perform the operation may be limited.

Chemical methods of female sterilization involving, for example, application of caustic chemicals within the Fallopian tubes are also known. The use of caustic chemicals as locally destructive agents has been attempted, but has been limited by concerns about safety and control of the delivery of various agents as well as other shortcomings due to the methods of application, e.g., blind placement of a particular solid chemical. For example, as described by Babcock, W., *Chemical Hysterectomy*, Jnl. Obstet. & Gyn., Vol. 7, p. 693 (1924), application of gauze strips soaked in a saturated solution of zinc chloride to the uterine walls has reportedly been used to induce amenorrhea, to cause sterility, and to treat tumors. However this procedure has several disadvantages. The application of the gauze strips is a blind procedure, however. The zinc chloride soaked gauze is packed in the uterus until the practitioner feels the cavity is full. The strips are left in place for a predetermined length of time and then removed. Delivery to and removal from the uterine cavity of the caustic gauze strips necessarily entails substantial risk of infection and of contacting the vaginal walls wherein the caustic could damage the vaginal and other tissue that are not the target of the treatment. Accordingly, successful use of this methodology requires substantial skill and experience, limiting the availability of the procedure to women with access to highly trained medical personnel.

Use of caustic agents such as silver nitrate, zinc chloride and copper sulfate has been studied for use in chemical sterilization by chemically cauterizing the Fallopian tubes. However, as discussed by Richart, R., *Female Transcervical Sterilization*, Chapter 3, Harper & Row (1983), even when massive tubal necrosis was achieved with the application of silver nitrate, a significant proportion of Fallopian tubes remained open. When compositions for the sustained release of the caustic agents such as silver nitrate (e.g., silver nitrate in alginic acid gel) were employed it was found that control over the release of the caustic agents was insufficient to avoid unacceptable side effects. Additionally, use of strong caustic agents such as acids and alkalies would require the concomitant use of equally strong neutralizing agents whose use is also laden with risk. Use of such agents also puts the practitioner in the difficult position of titrating the neutralization of the caustic agent in the patient's uterus and Fallopian tubes.

There exists, therefore, an ongoing need for improved methods for precision delivery of silver nitrate to the Fallopian tubes for chemical sterilization. The present invention provides such improved methods.

SUMMARY OF THE INVENTION

The present invention provides a method as well as a device for inducing Fallopian tube blockage as a means for female contraception. The method comprises contacting the inner surface tissue of a Fallopian tube with a device that provides at least one silver nitrate bearing solid or semi-solid substrate (e.g., a bead, an array of beads, suppository, braid, string, thread, paste, pellet, and the like) delivering an amount of silver nitrate to the tissue sufficient to induce blockage of the Fallopian tube. Preferably, the substrate is an array of beads on an elongated flexible carrier such as a braid, string, thread, suture, and the like. The bead can be round, ovoid, cylindrical or can have any other convenient shape. The silver nitrate bearing substrate is introduced through the uterine opening of the Fallopian tube by use of a catheter or other device suitable for manipulating the substrate. Preferably, a plurality of silver nitrate bearing beads is introduced into the Fallopian tube.

In a preferred device embodiment, one or more silver nitrate bearing beads are arranged on an elongated flexible carrier which is a strand segment such as string, monofilament, braid, multifilament thread, suture, or the like, to facilitate introduction and subsequent removal of the beads. The amount of silver nitrate delivered to the tissue is sufficient to induce tissue necrosis and blockage of the Fallopian tube. The silver nitrate is delivered to the tissue by the substrate in a controlled and localized manner, preferably to the interstitial region of the Fallopian tube.

The silver nitrate bearing bead can be a solid bead having silver nitrate coated on the surface of the bead. Alternatively, the silver nitrate bearing bead can be a porous bead having silver nitrate dispersed within pores of the bead. Porous beads can be rigid or resilient. The beads are preferably substantially spherical in shape and have an average diameter in the range of about 0.5 to about 2 millimeters. Alternatively, the beads can have projections such as protuberance, or spikes, to provide anchoring upon insertion. Preferably, when a plurality of beads are utilized, the beads are substantially uniform in size.

The total amount of silver nitrate delivered to a specific site in the Fallopian tube is an amount sufficient to necrose the tissue at that site and to produce a scar. Preferably, each bead is bears about 5 milligrams to about 100 milligrams of silver nitrate per bead.

In an alternative embodiment, the silver nitrate bearing bead can be replaced by a relatively viscous paste, a suppository, or a pellet. The paste, suppository, or pellet comprises an amount of silver nitrate sufficient to necrose the tissue of the interstitial region of the Fallopian tube, and thereby occlude the Fallopian tube.

In yet another embodiment of the present invention, the elongated flexible carrier itself supply silver nitrate, either alone or in combination with a bead or an array of beads on the carrier.

BRIEF DESCRIPTION OF THE DRAWINGS

FIG. 4 is a schematic cross-sectional view illustrating a string of substantially spherical silver nitrate bearing beads arrayed in a Fallopian tube of a human female according to the methods of the present invention.

FIG. 5 is a cross-sectional view of a bead having a silver nitrate-containing composition coated on the exterior surface of the bead.

FIG. 6 is a cross-sectional view of a porous bead having a silver nitrate-containing composition deposited within the pores of the bead.

FIG. 7 is a perspective view of a plurality of substantially spherical silver nitrate bearing beads arranged on a string, braid, thread, and the like;

FIG. 8 is a perspective view of a plurality of ovoid silver nitrate bearing beads arranged on a monofilament and including an anchoring mechanism at the end of the monofilament;

FIG. 9 is a perspective view of a plurality of substantially cylindrical silver nitrate bearing beads arranged on a monofilament as in FIG. 8, and including an alternative anchoring mechanism at the end of the monofilament.

DETAILED DESCRIPTION OF PREFERRED EMBODIMENTS

Figure 1:
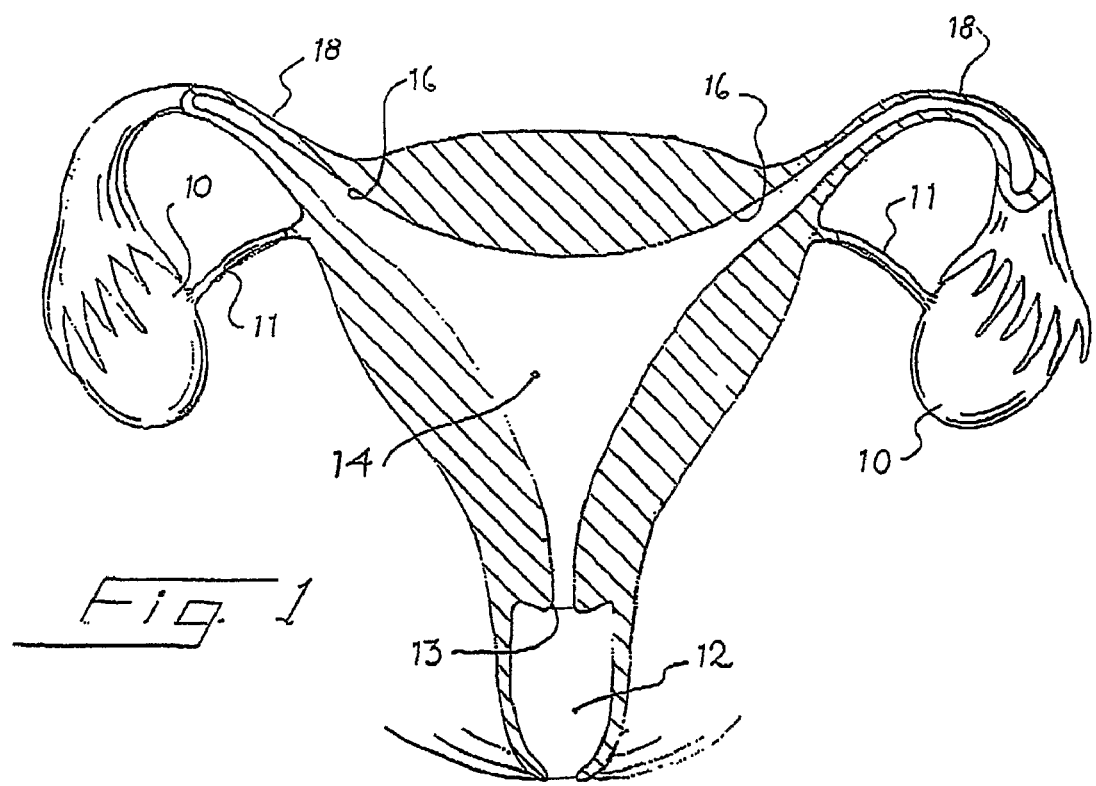
FIG. 1 provides a schematic cross-sectional view of the human female reproductive organs.

As used herein, the term "necrosis" and grammatical variations thereof means death of cells in a tissue. The term "chemical necrosis" and grammatical variations thereof means necrosis resulting from contact with a caustic chemical agent. The terms "physiologically inert" and "physiologically tolerable" as used herein and in the appended claims in references to materials or chemical components of silver nitrate delivery vehicles mean that the material or chemical component does not produce an adverse physiological reaction to the patient when present in the uterine cavity or Fallopian tubes of the patient. Adverse physiological reactions include, for example, allergic and other systemic reactions, local inflammation not attributable to the silver nitrate, and the like.

The present invention provides a method for inducing Fallopian tube blockage comprising contacting the inner surface tissue of a Fallopian tube with at least one silver nitrate bearing substrate, delivering an amount of silver nitrate to an interstitial region within the Fallopian tube sufficient to induce necrosis and produce scar tissue over at least about 10 millimeters along the length of the Fallopian tube. The present method provides a convenient and effective means for permanent female birth control by occluding the Fallopian tube to the extent that an ovum cannot pass beyond the occlusion into the uterus and sperm cannot pass beyond the occlusion to fertilize an ovum.

In a preferred embodiment of the present invention, at least one silver nitrate bearing bead is introduced through the opening from the uterus into the Fallopian tube by use of a catheter or other device suitable for manipulating the bead. Alternatively, a plurality of beads can be introduced into the Fallopian tube. Preferably, one or more silver nitrate bearing beads are arranged on a string, monofilament, or the like to facilitate later removal of the beads. The method of the present invention delivers an amount of silver nitrate to the tissue sufficient to cause tissue necrosis and blockage of the Fallopian tube. The silver nitrate is delivered to the tissue by the bead in a controlled and localized manner.

The beads can be constructed from any biocompatible material (e.g., nylon, such as Nylon-6 and the like, polyethylene, or sintered glass). Preferably the beads are porous to increase their silver nitrate loading capacity. The beads can be delivered, for example, by a catheter, preferably having a diameter of about 2 mm, and having a weakly sealed tip. The catheter can be preloaded with silver nitrate bearing beads, and can include a plunger for pushing the beads into the orifice of the Fallopian tube to a depth of about 2 to about 3 centimeters (i.e., into the interstitial region of the Fallopian tube). Alternatively, the catheter can include an inner catheter in which the beads are housed. After the tip of the outer catheter is placed within the orifice of the Fallopian tube, the inner catheter tube can be advanced to the proper depth and then withdrawn from around the beads, leaving the beads in place in the Fallopian tube. The catheter can be placed at the orifice of the Fallopian tube with the aid of an endoscope, with the aid of radiographical imaging, or in any other manner desired. Preferably, the beads are arranged on a string or filament to facilitate their eventual removal. If the bead substrate is fully biocompatible, the beads may be left permanently embedded in the scar tissue that forms as a result of silver nitrate induced necrosis.

Silver nitrate bearing beads can be of any shape suitable for insertion into the interstitial region of the Fallopian tubes. Preferably, the silver nitrate bearing beads are atraumatic and substantially spherical, ovoid or cylindrical in shape.

FIG. 1 provides a schematic cross-sectional view of the human female reproductive organs. In FIG. 1, vagina 12 terminates where cervix 13 leads into the uterus 14. Openings 16 in uterus 14 lead into Fallopian tubes 18. Ovaries 10 are located at the distal end of Fallopian tubes 18 and are connected thereto by ligament 11.

Figure 1A:
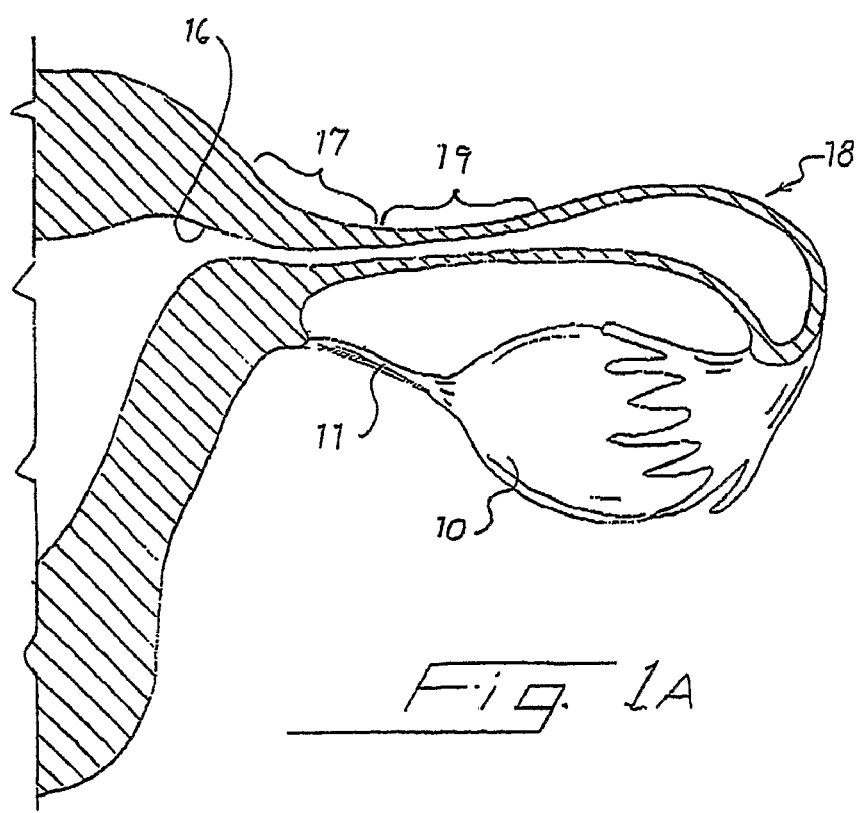
FIG. 1A is an enlarged detail view of the human female reproductive organs showing the region of the Fallopian tube.

FIG. 1A shows an enlarged cross-section in the region of the Fallopian tube. The interstitial region 17 of Fallopian tube 18 is situated between opening 16 and isthmic region 19.

Figure 2:
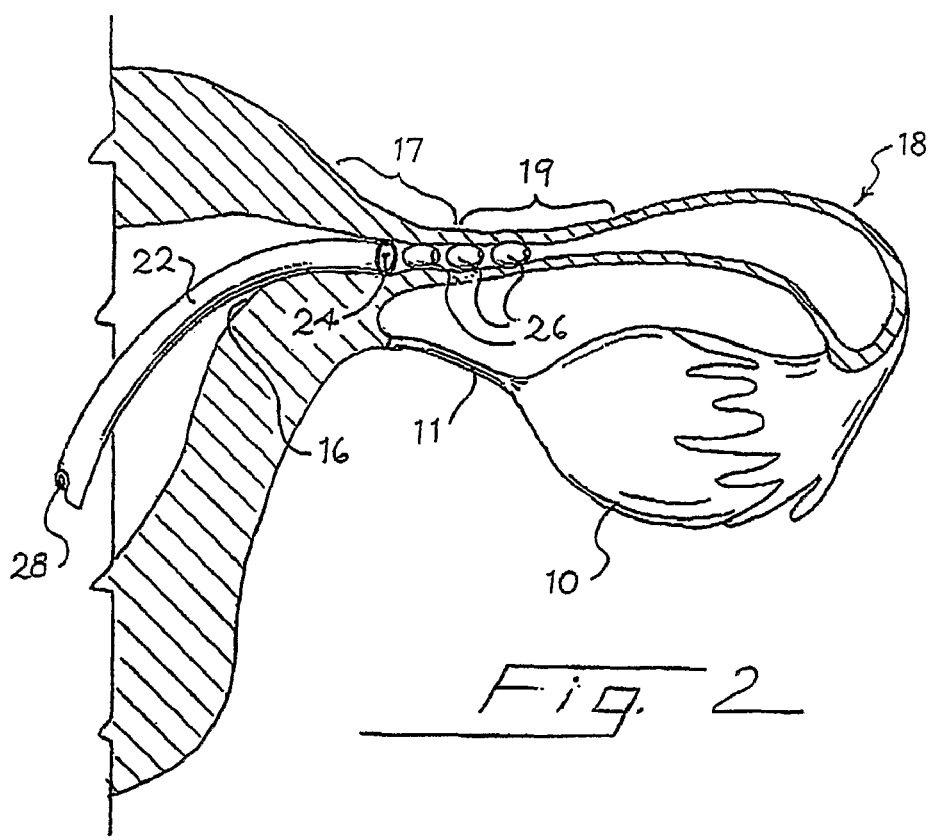
FIG. 2 is a schematic cross-sectional view of the human female reproductive organs illustrating delivery of a silver nitrate bearing bead into a Fallopian tube using a catheter.

FIG. 2 is a schematic cross-sectional view of the human female reproductive organs illustrating delivery of a silver nitrate bearing bead into a Fallopian tube using a catheter. Distal end 24 of catheter 22 is disposed just anterior to opening 16 leading into Fallopian tube 18. Silver nitrate bearing beads 26 are disposed within Fallopian tube 18 for delivery of silver nitrate to the interior of Fallopian tube 18. Beads 26 are sized to pass through the interior passage 28 of catheter 22 for placement of beads 26 into Fallopian tube 18.

Figure 3:
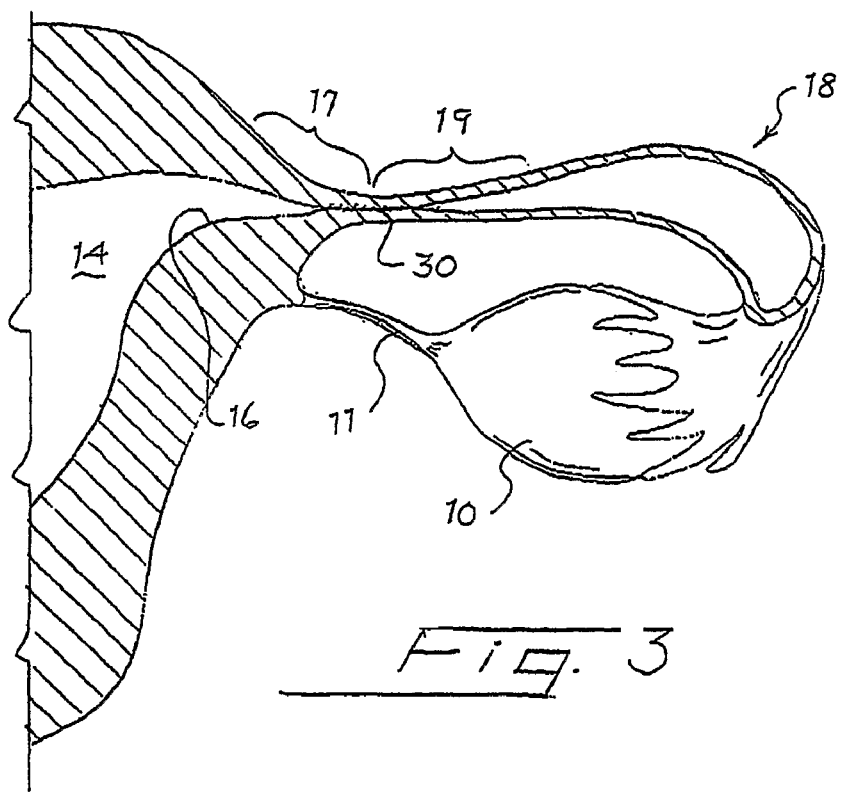
FIG. 3 is a schematic cross-sectional view of the human female reproductive organs showing blockage of the Fallopian tube after treatment by the method of the present invention.

FIG. 3 is a schematic cross-sectional view of the Fallopian tube 18 showing blockage 30 after silver nitrate has been delivered to Fallopian tube 18 by the method of the invention. Blockage 30 substantially completely occludes Fallopian tube 18 in the interstitial region 17 so that no ova can pass from ovary 10 into uterus 14 and no sperm can pass from uterus 14 beyond blockage 30.

FIG. 4 is a schematic cross-sectional view illustrating a device comprised of a plurality of interconnected silver nitrate bearing beads 32 arrayed along a flexible elongated carrier such as a segment of a string or monofilament 34 positioned in Fallopian tube 18 of a human female. String or monofilament 34 facilitates removal of beads 32 after treatment is complete, and optionally, can carry some of the silver nitrate.

The silver nitrate bearing bead can be a solid bead having silver nitrate coated on the surface of the bead. Alternatively, the silver nitrate bearing bead can be a porous bead having a solid silver nitrate composition dispersed within pores of the bead. Porous beads can be rigid or resilient. The beads are preferably substantially spherical in shape and have an average diameter in the range of about 0.5 to about 2 millimeters. Preferably, when a plurality of beads is utilized, the beads are substantially uniform in size. A string, thread or braid carrying the beads can also be impregnated with the silver nitrate composition, if desired. Alternatively, a segment of an elongated flexible carrier such as a strong, thread, braid and the like, can be the sole source of the silver nitrate composition.

Solid silver nitrate-containing compositions for coating or filling beads adhere firmly to the carrier and the beads, but readily release silver nitrate when contact with the moist tissue within the Fallopian tubes. The solid silver nitrate-containing composition can be coated on the external surface of a bead, or can be present at least partially within a porous bead, as described above.

Preferably the silver nitrate bearing beads are substantially spherical in shape and have an average diameter in the range of about 0.25 to about 2 millimeters, more preferably about 0.5 to about 1.5 millimeters.

In the case of ovoid-shaped beads, preferably the smaller diameter of the ovoid is in the range of about 0.25 to 2 millimeters. In the case of cylindrical-shaped beads, preferably the diameter of the bead is in the range of about 0.5 to 2 millimeters and the length is in the range of about 0.5 to about 5 millimeters.

The beads can be made of any physiologically tolerable material that can meet governmental regulatory requirements, such as United States Food and Drug Administration requirements for medical devices which are received within the uterine cavity. The bead can be composed of a physiologically inert polymer such as polystyrene, polyethylene, polypropylene, nylon, polyethylene terephthalate (PET), polyurethane, ethylene/vinyl acetate copolymers, poloxamers, and the like. Alternatively, the beads can be made of a physiologically inert ceramic, ion exchange resins, of stainless steel, or the like inert material. In one preferred embodiment, the beads are made of a resorbable or biodegradable material, such as a polylactic acid, a polyglycolic acid, a lactic acid-glycolic acid copolymer, and the like.

The beads can be perforated, spongiform, porous, or non-porous. Porous beads can be polymeric foam beads, such as polypropylene foam or polyethylene foam beads, or can be beads having machined pores or perforations, molded pores, molded indentations or grooves, and the like. Perforations or pores in the beads, as well as indentations or grooves, when present, can increase the loading of silver nitrate carried by the beads. For example, the beads can include one or more through perforations which can be filled with a silver nitrate-containing composition. Alternatively, the beads can have cavities or pits in the surface of the beads to hold additional silver nitrate therein. The beads can include a magnetic material, if desired, to facilitate recovery of the beads after treatment is terminated.

In a preferred embodiment, at least one silver nitrate bearing bead is arranged on a string or monofilament to facilitate easy removal of the beads from the Fallopian tube when treatment is complete or needs to be terminated.

In an alternative embodiment, the silver nitrate-bearing beads can be replaced by a relatively viscous paste, a suppository or a pellet comprising silver nitrate. The paste, suppository or pellets delivered to the interstitial region of the Fallopian tube include sufficient silver nitrate to necrose the tissue and occlude the tube. When a paste is used as a substrate for the silver nitrate, the paste preferably has a viscosity, at normal body temperature, similar to that of tooth paste, e.g., about 120,000 to about 300,000 centipoise (Brookfield). Preferably, the paste is non-thixotropic.

The silver nitrate bearing moieties can be manufactured by a variety of methods known in the art. For example, the beads can be coated with a molten silver nitrate containing composition, such as substantially pure silver nitrate, or a mixture of at least about 60 weight percent silver nitrate and up to about 40 weight percent of a diluent such as an alkali metal nitrate, e.g., potassium nitrate, preferably no less than about 5 percent by weight of alkali metal nitrate. The presence of the alkali metal nitrate in these compositions appears to improve the physical properties of the resulting solid solution e.g., dispersion and dissolution of the silver nitrate present. The molten composition can be deposited on the beads by spraying, for example, by spraying a molten silver nitrate composition onto a fluidized bed of beads, or poured into a mold cavity in which the beads have been placed. The beads also can be coated by mixing the beads with a molten silver nitrate composition in a rotating kiln, a pin blender, and the like. Pure silver nitrate melts at a temperature of about 212° C. When a molten silver nitrate composition is deposited on a bead, preferably the bead and/or braid, thread, string, or the like, has a melting point above the melting point of the silver nitrate composition. Preferred silver nitrate compositions are $AgNO_3/KNO_3$ solid solutions containing at least 50 mol-percent $AgNO_3$ preferably 80-90 mol percent $AgNO_3$.

Alternatively, an aqueous composition containing silver nitrate and a binder can be deposited on the beads, or the beads impregnated therewith, and dried to provide silver nitrate delivery vehicles of the present invention. The aqueous composition can be a paste or a fluid containing a thickening binder (e.g., a dextran), such as are described in U.S. Pat. No. 6,197,351 to Neuwirth, the relevant disclosures of which are incorporated herein by reference. Other suitable binders include any physiologically tolerable binder, such as synthetic polymeric binders and thickeners (e.g., poloxamer polymers, carbomer polymers, polyvinylpyrrolidone, and the like), gelatin, hardened gelatin, polysaccharides (e.g., dextrans, microcrystalline cellulose, xanthan gum, guar, gum, and the like), and like thickening and binding agents, so long as they are of a grade suitable for use in intrauterine preparations. Pharmaceutically acceptable binders, carriers, diluents, disintegrants, and the like are described in *Remington's Pharmaceutical Sciences,* 14th Ed., Mack Publishing Co., pp. 1650-1653 (1970), the relevant disclosures of which are incorporated herein by reference to the extent pertinent.

In one coating method, the silver nitrate-containing composition can be an aqueous composition comprising silver nitrate and a polymeric binder such as polyvinylpyrrolidone, and the like. The composition can be applied to the beads in any suitable manner. Preferably, the composition is applied as a uniform coating having a relatively smooth surface structure and a relatively constant thickness. For example, the composition may be applied to the beads by utilizing a pneumatic spray gun, by dipping, and the like expedients. Ideally, spraying is continuous, with substantially concurrent drying so that the beads do not become too moist (overly wet and stick together). The freshly sprayed silver nitrate coating is dried as quickly as possible to avoid agglomeration of the beads. Other suitable methods include the use of fluidized-bed processes to coat the beads with a silver nitrate composition while suspended in a stream of gas, preferably an inert gas. Modified coating drums (e.g., cylindrical horizontally rotating units with a perforated wall) are also suitable for coating the beads with silver nitrate.

In another embodiment, solid silver nitrate, as a powder or fine crystals, can be added as a filler to a polymer melt, optionally with a blowing agent, during the bead-making process. Beads of silver nitrate filled polymer can then be extruded to form a silver nitrate delivery vehicle comprising a porous bead with silver nitrate dispersed therein. Preferably the bead is water swellable or water permeable, so that silver nitrate in the interior of the bead can be released when the beads are in contact with the moist tissue in the interstitial region of a Fallopian tube. Alternatively, an aqueous silver nitrate solution can be imbibed into a preformed, porous, water swellable or water permeable polymer bead.

FIG. 5 is a cross-sectional view of a silver nitrate bearing bead 100, comprising a polymeric bead 112, such as a polypropylene or polystyrene bead, having a layer 114 of silver nitrate dispersed in polyvinylpyrrolidone deposited on the surface of bead 112. FIG. 6 is a cross-sectional view of a silver nitrate bearing bead 200 comprising a porous polymeric bead 220 having silver nitrate 240 within the pores 250 of bead 220. FIG. 7 shows a plurality of silver nitrate bearing beads 300 arranged on string or thread 320, terminated by knots 340 and 342 to facilitate removal of beads 300 after treatment of a Fallopian tube by the methods of the present invention.

FIG. 8 illustrates an alternate embodiment of the present invention. An array 400 of silver nitrate coated beads is arranged on a nylon monofilament 420 that terminates in a flexible, harpoon-like distal end portion 422. The distal end portion 422 is provided with harpoon point head 424 having a pair of tines 426 that are sufficiently flexible to collapse during insertion into a Fallopian tube and to invert as shown by the phantom lines when a pulling force is applied to monofilament 420. In this manner, the bead array 400 can be readily removed from a Fallopian tube when necessary or desired, but otherwise is held in place by point head 424. Retainer 428 such as a relatively smaller bead fused to monofilament 420 holds bead array 400 on monofilament 420 in place between point head 424 on distal end portion 422 and retainer 428 on or near proximal end portion 430 of monofilament 420.

Alternatively, tines 426 of FIG. 8 can be replaced with a flexible, invertible disc or cup, as shown in FIG. 9. Array 500 of silver nitrate bearing beads is arranged on a nylon monofilament 520 that terminates in a flexible, cup-like distal end portion 522. The distal end portion 522 is provided with an invertible cup-like disk 526 that is sufficiently flexible to collapse during insertion into a Fallopian tube and to invert as shown by the phantom lines when a pulling force is applied to monofilament 520. In this manner, the bead array 500 can be readily removed from a Fallopian tube when necessary or desired, but otherwise is held in place by disk 526. Retainer 528, such as a relatively smaller bead fused to monofilament 520, holds bead array 500 on monofilament 520 in place between disk 526 on distal end portion 522 and retainer 528 on or near proximal end portion 530 of monofilament 520.

Porous beads preferably have an open cell structure and are composed of a hydrophilic polymer which is water permeable such as nylon, for example, or have surfaces that are hydrophilic.

Blowing agents that can be used to form porous polymeric materials are well known in the art. Suitable blowing agents and methods of manufacturing foamed polymeric materials are described in Frados, *Plastics Engineering Handbook of the Society of Plastics Industry, Inc.*, Chapter 20, Van Nostrand Reinhold Co., New York, pp. 499-599 (1976). Suitable blowing agents include, for example, chemical blowing agents such as azobisisobutyronitrile, azodicarbonamide, and the like; and gases such as carbon dioxide, nitrogen, and the like.

The silver nitrate bearing beads delivered to the Fallopian tubes include a sufficient quantity of silver nitrate to produce the level of tissue necrosis sufficient to substantially completely occlude the Fallopian tube. Preferably a sufficient number of beads is administered to the Fallopian tubes to provide a total quantity of silver nitrate in the range of about 5 to about 500 milligrams, preferably about 10 to about 150 milligrams. Preferably, each bead can release an amount of silver nitrate in the range of about 3 to about 50 milligrams.

As stated hereinabove, the delivery vehicle for the silver nitrate composition into the Fallopian tubes can be a segment of an elongated flexible carrier. Such a carrier can be a strand of a biocompatible material such as a braid, thread, filament, yarn, and the like, impregnated with a silver nitrate composition. A predetermined length of a segment of such an impregnated strand can be introduced into the Fallopian tubes to induce the desired necrosis.

Figures 10, 11:
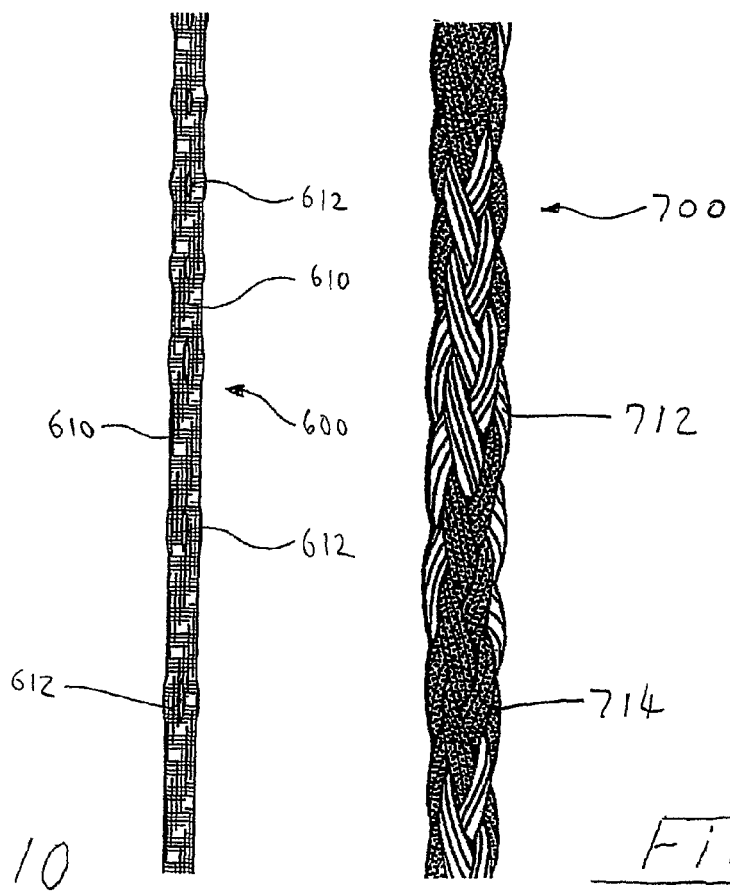
FIG. 10 shows a strand segment which is a woven braid impregnated with a silver nitrate composition and provided with optional spaced pockets for receiving pellets that contain silver nitrate.
FIG. 11 shows a strand segment which is a braid made up of filaments that are impregnated or coated with a silver nitrate composition as well as filaments that are free from silver nitrate.

FIG. 10 illustrates a strand segment 600 which is a woven braid 610 impregnated with a silver nitrate composition and provided with open pockets 612 that can carry pellets of a silver nitrate composition.

FIG. 11 illustrates a strand segment 700 which is a braid 712 constituted by interwoven filaments 714 and 716. Filaments 714 do not carry any silver nitrate, but filaments 716 are impregnated with a silver nitrate composition. The relative diameters of strand segments 600 and 700 shown in respective FIGS. 10 and 11 are illustrative only inasmuch as the strand diameters are selected depending upon a particular application. Usually, the strand diameters are in the range of about 0.5 to 1.5 millimeters.

EXAMPLE 1

Preparation of $AgNO_3$ Bearing Beads

A. Preparation of Coating Solutions.

Coating Solution A was prepared by dissolving about 1 gram of silver nitrate in about 4 milliliters of water and adding thereto a solution of about 0.4 grams of polyvinylpyrrolidone (K-120) in about 4 milliliters of water.

Coating Solution B was prepared by adding about 4 milliliters of 70% denatured ethanol to about 8 milliliters of Coating Solution A.

B. Coating of Beads (i) Polypropylene beads having a diameter of about 3 millimeters and perforated polystyrene beads having a diameter of about 5 millimeters were soaked in Coating Solution A for about 2 minutes, removed from the coating solution, and were dried at ambient room temperature for about 30 minutes. The perforated polystyrene beads had single, substantially cylindrical through perforation having a diameter of about 1 millimeter in each bead.

(ii) Polyethylene and polystyrene beads as described in (i) above were soaked in Coating Solution B for about 2 minutes, removed from the coating solution, and were dried at ambient room temperature for about 30 minutes.

(iii) The surfaces of polypropylene and perforated polystyrene beads as described in (i) above were roughened and the beads were then coated with Coating Solution A as described in (I) above. The surface of each bead was roughened by rolling the bead under a file using a circular oscillating motion (about 25 oscillations) followed by rolling the bead under an emery board using a circular oscillating motion (about 50 oscillations).

(iv) Surface roughened polypropylene and polystyrene beads as described in (iii) above were soaked in Coating Solution B for about 2 minutes, removed from the Coating Solution, and were dried at ambient temperature for about 10 minutes. The beads were then returned to the Coating Solution B for about 1 minute, removed, and dried for an additional 10 minutes. Finally, the twice-coated beads were returned to Coating Solution B for about 1 minute, removed from the solution, and were dried at ambient room temperature for about 30 minutes.

(v) Nylon 6 beads about 2 mm in diameter were injected molded on a polyethylene terephthalate (PET) suture (Ethibond 4.0) and coated with coating solution A as stated above.

(vi) Nylon 6 beads about 2 mm in diameter molded on PET suture (Ethibond 4.0), were roughened as in (iii) above and coated with a coating Solution A, as stated above.

EXAMPLE 2

Tissue Necrosis with AgNO$_3$ Bearing Beads

Silver nitrate bearing beads prepared in Example 1 were placed on the surface of beef muscle tissue (fillet mignon). Beads without a silver nitrate coating were also placed on the tissue as negative controls, as was a crystal of pure silver nitrate (about 1 mm diameter by 3 mm length; as a positive control).

The surface of the tissue under each bead was observed at about 5 minute intervals for a total of about 15 to about 20 minutes. The degree of necrosis of the tissue under each bead was noted at each observation. The degree of necrosis was rated as follows:

slight visible pitting of the tissue surface (+); moderate pitting of tissue surface with slight blackening of the tissue (++); significant pitting with moderate blackening of the tissue (+++); severe pitting with complete blackening of the tissue (++++); severe pitting with complete blackening of the tissue, spreading beyond the point of contact (+++++); and no observed necrosis (---)

TABLE 1

| | Tissue Necrosis | | | |
|---|---|---|---|---|
| | Time (Minutes) | | | |
| Bead Batch | 5 | 10 | 15 | 20 |
| AgNO$_3$ Crystal | +++ | ++++ | +++++ | +++++ |
| PP Control | --- | --- | --- | --- |
| PS Control | --- | --- | --- | --- |
| Smooth Surface | | | | |
| PP (i) | + | N/A | ++ | ++$^a$ |
| PS (i) | + | N/A | ++ | ++$^b$ |
| PP (ii) | + | ++ | +++ | N/A$^c$ |
| PS (ii) | ++ | +++ | ++++ | N/A$^a$ |
| N6 (v) | + | ++ | +++ | ++++ |
| Rough Surface | | | | |
| PP (iii) | ++ | +++ | ++++ | N/A$^a$ |
| PS (iii) | ++ | +++ | ++++ | N/A$^a$ |
| PP (iv) | + | + | ++ | N/A$^a$ |
| PS (iv) | + | ++ | +++ | N/A$^a$ |
| N6 (vi) | + | ++ | +++ | ++++ |

PP = polypropylene;
PS = polystyrene;
N6 = Nylon 6
$^a$= bead penetrated the tissue about ½ the diameter of the bead
$^b$= bead penetrated the tissue about ¼ of the diameter of the bead
$^c$= bead penetrated about ⅓ the diameter of the bead.

The degree of tissue necrosis observed for each bead type is recorded in Table 1. The data in Table 1 indicate that the silver nitrate coated beads as described herein provide an effective vehicle for delivering a tissue necrosing amount of silver nitrate to mammalian tissue.

The foregoing description is to be taken as illustrative, but not limiting. Still other variants within the spirit and scope of the present invention, including other uses for silver nitrate bearing beads, will readily present themselves to those skilled in the art.

The invention claimed is:

1. A method of inducing Fallopian tube blockage consisting essentially of contacting the interior of a Fallopian tube with at least one silver nitrate bearing bead, and delivering into the Fallopian tube an amount of silver nitrate sufficient to induce tissue necrosis and occlusion of the Fallopian tube.

2. The method of claim 1 wherein the at least one bead comprises a material selected from the group consisting of a polymer, a ceramic, and stainless steel.

3. The method of claim 2 wherein the polymer is selected from the group consisting of polystyrene, polyethylene, polypropylene, nylon, polyurethane, ethylene/vinyl acetate copolymer, and polyethyleneterephthalate.

4. The method of claim 1 wherein the at least one bead is porous.

5. The method of claim 1 wherein the at least one bead is perforated.

6. The method of claim 1 wherein the silver nitrate is deposited on the surface of the at least one bead.

7. The method of claim 1 wherein at least a portion of the silver nitrate is contained within the at least one bead.

8. The method of claim 1 wherein the at least one bead is substantially spherical and have an average diameter in the range of about 0.25 to about 2 millimeters.

9. The method of claim 1 wherein the silver nitrate is present as a composition that comprises at least about 60 percent by weight silver nitrate.

10. The method of claim 1 wherein the silver nitrate is present as a composition that comprises up to about 40 percent by weight alkali metal nitrate.

11. The method of claim 1 wherein the silver nitrate is present in a physiologically tolerable binding matrix.

12. The method of claim 11 wherein binding matrix is selected from the group consisting of a synthetic polymeric binder, a gelatin binder, a polysaccharide binder, and a combination thereof.

13. The method of claim 1 wherein the at least one silver nitrate bearing bead is attached to a string to facilitate removal of the bead from the Fallopian tube.

14. The method of claim 1 wherein an array of silver nitrate bearing beads is contacted with the interior tissue of the Fallopian tube.

15. The method of claim 14 wherein the array of beads is arranged on a elongated flexible carrier.

16. A method of inducing Fallopian tube blockage consisting essentially of contacting the interior of the Fallopian tube with a solid or semi-solid substrate bearing silver nitrate in an amount sufficient to necrose tissue and occlude the Fallopian tube.

17. The method of claim 16 wherein the substrate is a bead, a relatively viscous paste, a suppository or a pellet.

18. The method of claim 16 wherein the substrate is an elongated flexible carrier.

19. The method of claim 16 wherein the substrate is a string.

20. The method of claim 16 wherein the substrate is a braid.

* * * * *